United States Patent [19]
Sorensen

[11] Patent Number: 5,843,698
[45] Date of Patent: Dec. 1, 1998

[54] DELETERIOUSLY AFFECTING MEMBERS OF A TARGET SPECIES BY EXPOSURE TO A COMPONENT OF SYMBIONT OR FOOD SOURCE OF AN ADJOINER SPECIES THAT IS SYMBIOTIC WITH THE TARGET SPECIES

[75] Inventor: Jens Ole Sorensen, Cayman Kai, Cayman Islands

[73] Assignee: Universal Ventures, Cayman Islands

[21] Appl. No.: 846,670

[22] Filed: Apr. 30, 1997

[51] Int. Cl.$^6$ .................. C12Q 1/02; C12Q 1/00
[52] U.S. Cl. .................. 435/29; 435/4; 435/5; 435/7.21; 435/7.22; 435/7.23; 435/253.1; 435/253.3; 426/665; 426/231
[58] Field of Search .................. 435/29, 4, 5, 7.21, 435/7.22, 7.23, 253.1, 253.3; 426/665, 231

[56] References Cited

U.S. PATENT DOCUMENTS

| | | | |
|---|---|---|---|
| 4,878,891 | 11/1989 | Judy et al. | 435/29 |
| 5,439,924 | 8/1995 | Miller | 435/29 |
| 5,527,700 | 6/1996 | Kaslow et al. | 435/29 |

OTHER PUBLICATIONS

Blakely, "The Good Virus", Discover, Nov. 1996, p. 50 et seq.
Hall, "Eat To Fight Cancer," Health, Apr. 1997, p. 108 et seq.

*Primary Examiner*—Louise N. Leary
*Attorney, Agent, or Firm*—Edward W. Callan

[57] ABSTRACT

A component of a member of a test species that deleteriously affects a target species that is a parasite of a given adjoiner species is identified by a method including a step (a) of separating at least one member of a test species that is a symbiont or a traditional food source of the given adjoiner species into a plurality of components; a step (b) of exposing at least some of the separated components of the member(s) of the test species separately to members of the target species; and a step (c) of examining such exposures to determine for such identification whether members of the target species have been deleteriously affected by such exposures; wherein steps (a), (b) and (c) are executed methodically and systematically. A product including such a test-species component identified as deleteriously affecting members of a target species and/or an equivalent of the identified component is manufactured either by separating the identified component in bulk quantities from members of the test species or by synthesizing the identified component and/or an equivalent of the identified component in bulk quantities. The product is tested to determine the extent of any deleterious effect upon the adjoiner species and the extent of the deleterious effect of the product upon the target species. The method of manufacturing the product may further include modifying the product to decrease any deleterious effect upon the adjoiner species and/or modifying the product to increase the deleterious effect upon the target species.

40 Claims, 3 Drawing Sheets

```
                    TEST SPECIES
    ┌─────────────────────────────────────────────┐
    │ SYMBIONT OF AN ADJOINER SPECIES TO THE TARGET SPECIES │──11
    ├─────────────────────────────────────────────┤
    │ TRADITIONAL FOOD SOURCE OF THE ADJOINER SPECIES │
    └─────────────────────────────────────────────┘
                          │
                          ▼
         EXPOSE TARGET-SPECIES COMPONENT ──30
           TO A TEST-SPECIES MEMBER
                          │
                          ▼
         SEPARATE THE TEST-SPECIES ──32
           MEMBER INTO COMPONENTS
                          │
                          ▼
         EXPOSE SEPARATED TEST-SPECIES ──34
         COMPONENTS TO THE TARGET SPECIES        FIG. 3
                          │
                          ▼
      EXAMINE EXPOSURE TO DETERMINE WHETHER THE ──36
      TARGET SPECIES HAS BEEN DELETERIOUSLY AFFECTED
```

```
              40                              42
    SEPARATE IDENTIFIED           SYNTHESIZE IDENTIFIED
    COMPONENT FROM                COMPONENT OR EQUIVALENT
    TEST SPECIES IN               OF IDENTIFIED COMPONENT
    BULK QUANTITIES               IN BULK QUANTITIES
             │                              │
    44       └──────────────┬───────────────┘      46
    ▼                                              ▼
    MODIFY TO DECREASE              MODIFY TO INCREASE
    DELETERIOUS EFFECT UPON         DELETERIOUS EFFECT
    ADJOINER SPECIES                UPON TARGET SPECIES
```

DELETERIOUSLY AFFECTING MEMBERS OF A TARGET SPECIES BY EXPOSURE TO A COMPONENT OF SYMBIONT OR FOOD SOURCE OF AN ADJOINER SPECIES THAT IS SYMBIOTIC WITH THE TARGET SPECIES

BACKGROUND OF THE INVENTION

The present invention generally pertains to materials that deleteriously affect members of a target species and is particularly directed to identifying, manufacturing, testing and using such materials.

It has been known to identify components of members of test species that deleteriously affect members of a target species by a method including the steps of:

(a) separating at least one member of each of a plurality of test species into a plurality of components;

(b) exposing at least some of said separated components of said member(s) of the test species separately to members of the target species; and (c) examining said exposures to determine for said identification whether members of the target species have been deleteriously affected by said exposures.

This method has been conducted to identify materials that are deleterious to a target species that is a symbiont of an adjoiner species, such as a parasite of the adjoiner species. Although such identification method has been practiced with test species that are symbionts or traditional food sources of the adjoiner species, it is believed that such symbiotic relationship and such food-source relationship between the test species and the adjoiner species have been merely incidental to broad screenings of a plurality of different test species based upon their chemical compositions rather than an intentional aspect of the method. A food source includes plants and animals and secretions and waste products therefrom, such as honey, pollen, sap, milk, feces and urine.

Symbiotic relationships between different species include (a) a parasitic relationship, wherein one species benefits from the relationship and the other species is harmed by the relationship; (b) mutualism, wherein both species benefit from the relationship; (c) commensalism, wherein one species benefits from the relationship and the other species is unaffected by the relationship; and (d) amensalism, wherein one species is harmed by the relationship and the other species is unaffected by the relationship.

SUMMARY OF THE INVENTION

The present invention provides a method of identifying components of members of test species that deleteriously affect members of a target species, comprising the steps of:

(a) separating at least one member of a test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (a), (b) and (c) are executed methodically and systematically with a large number of test species that are symbionts or traditional food sources of the adjoiner species.

In another aspect of the present invention, step (a) is executed with such a large number of test species that are symbionts or traditional food sources of the adjoiner species that the ratio of execution of step (a) when the test species are symbionts or traditional food sources of the adjoiner species relative to execution of step (a) when the test species are not symbionts or traditional food sources of the adjoiner species is significantly higher than said ratio of execution according to the prior art.

In a further aspect of the present invention, wherein step (a) comprises separating at least one member of each of a plurality of test species into a plurality of components, steps (b) and (c) are executed in such large numbers when the test species are symbionts or traditional food sources of the adjoiner species that the ratio of execution of steps (b) and (c) when the test species are symbionts or traditional food sources of the adjoiner species relative to execution of steps (b) and (c) when the test species are not symbionts or traditional food sources of the adjoiner species is significantly higher than said ratio of execution according to the prior art.

In an additional aspect, the present invention provides a method of identifying components of members of a test species that deleteriously affect members of a target species, comprising the steps of:

(a) separating at least one member of the test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (b) and (c) are executed in such large numbers when the test species is a symbiont or a traditional food source of the adjoiner species that the ratio of execution of steps (b) and (c) when the test species is a symbiont or a traditional food source of the adjoiner species relative to execution of steps (b) and (c) when the test species is not a symbiont or a traditional food source of the adjoiner species is significantly higher than said ratio of execution according to the prior art.

In a still another aspect, the present invention provides a method of identifying components of members of a test species that deleteriously affect members of a target species, comprising the steps of:

(a) identifying the test species as a symbiont or a traditional food source of a given adjoiner species when the test species had not been known to be a symbiont or a traditional food source of the given adjoiner species;

(b) separating at least one member of the test species into a plurality of components;

(c) exposing at least some of said separated components of said member(s) of the test species separately to members of the target species, wherein the target species is a symbiont source of the adjoiner species; and (d) examining said exposures to determine for said identification whether members of the target species have been deleteriously affected by said exposures.

In a yet another aspect, the present invention provides a method of identifying components of members of a test species that deleteriously affect members of a target species, comprising the steps of:

(a) exposing at least a component of at least one member of the target species to at least one member of the test species;

(b) subsequent to step (a), separating said exposed at least one member of the test species into a plurality of components;

(c) exposing at least some of said separated components of said member(s) of the test species separately to members of the target species, wherein the target species is a symbiont of an adjoiner species and the test species is a symbiont or a traditional food source of the adjoiner species; and (d) examining said exposures to determine for said identification whether members of the target species have been deleteriously affected by said exposures.

The present invention provides each separated component of a member of a test species identified by any of the above-described identification methods as deleteriously affecting members of a target species or an equivalent of said identified component.

The present invention further provides methods of manufacturing products including a test-species component identified by any of the foregoing methods as deleteriously affecting members of a target species and/or an equivalent of said identified component, as described below in the detailed description of the preferred embodiments.

The present invention also provides products manufactured according to such methods of manufacture.

The present invention additionally provides methods of using and testing products manufactured according to such methods of manufacture, as described below in the detailed description of the preferred embodiments.

Additional features of the present invention are described with reference to the detailed description of the preferred embodiments.

DETAILED DESCRIPTION

In the various embodiments of the present invention described herein, the adjoiner species include but are not limited to the human species, a species having a near-human-species genetic composition, such as chimpanzees and pigs, and other species afflicted with parasitic diseases; the target species include but are not limited to HIV (the AIDS-causing virus), cancer causing viruses, *E. coli* bacteria, histoplasma capsulatum (which causes histoplasinosis), borrelia burgdoferi (which causes Lime's disease), the typhoid fever causing virus, the Norwalk virus and the rotovirus; and the test species include but are not limited to plasmodium falciparum, plasmodium ovale, plasmodium vivax, and plasmodium malariae (all four of which are species of malaria), treponema pallidum (syphilis), the smallpox virus, mycobacterium tuberculosis, ascaris lumbricoides (tapeworm), deratophyte (athlete's foot), helicobacter pylori (ulcer-causing bacteria) and traditional food sources of the adjoiner species, including co-evolutionary food sources of the adjoiner species that previously had not been known to be food sources of the adjoiner species.

Figure 1:
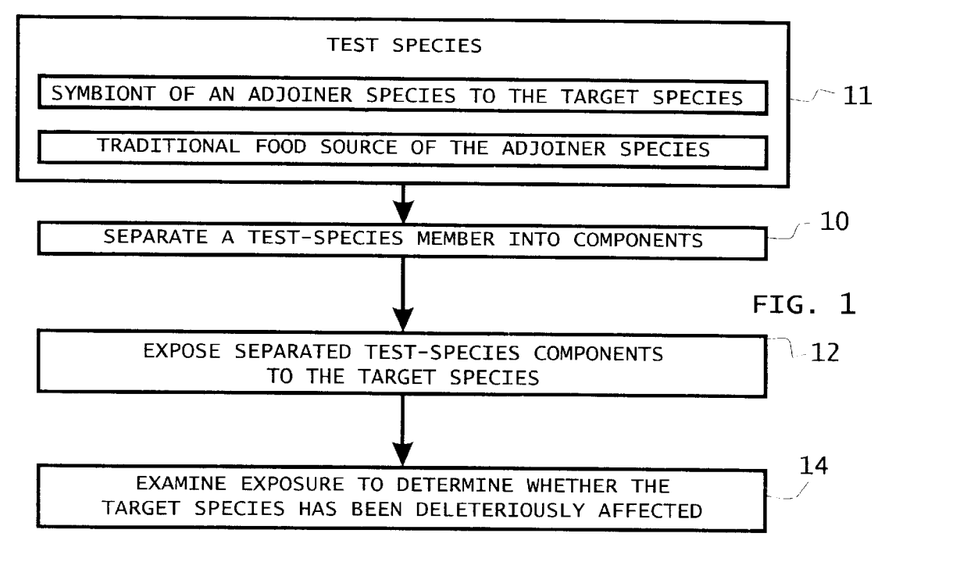
FIG. 1 is a block diagram of one preferred embodiment of the identification method of the present invention.

Referring to FIG. 1, one preferred embodiment of the method of the present invention of identifying components of members of test species that deleteriously affect members of a target species that is a symbiont of a given adjoiner species includes a step 10 of separating at least one member of a test species that is a symbiont or a traditional food source of the given adjoiner species into a plurality of components; a step 12 of exposing at least some of the separated components of the member(s) of the test species separately to members of the target species; and a step 14 of examining such exposures to determine for such identification whether members of the target species have been deleteriously affected by such exposures; wherein the separation step 10, the exposure step 12 and the examination step 14 are executed methodically and systematically with a large number of test species that are symbionts or traditional food sources of the adjoiner species.

In some preferred embodiments, the separation step 10 is executed with such a large number of test species that are symbionts or traditional food sources of the adjoiner species that the ratio of execution of the separation step 10 when the test species are symbionts or traditional food sources of the adjoiner species relative to execution of the separation step 10 when the test species are not symbionts or traditional food sources of the adjoiner species is significantly higher than said ratio of execution according to the prior art.

In some preferred embodiments, the exposure step 12 and the examination step 14 are executed in such large numbers when the test species are symbionts or traditional food sources of the adjoiner species that the ratio of execution of the exposure step 12 and the examination step 14 when the test species are symbionts or traditional food sources of the adjoiner species relative to execution of steps the exposure step 12 and the examination step 14 when the test species are not symbionts or traditional food sources of the adjoiner species is significantly higher than said ratio of execution according to the prior art.

Figure 2:
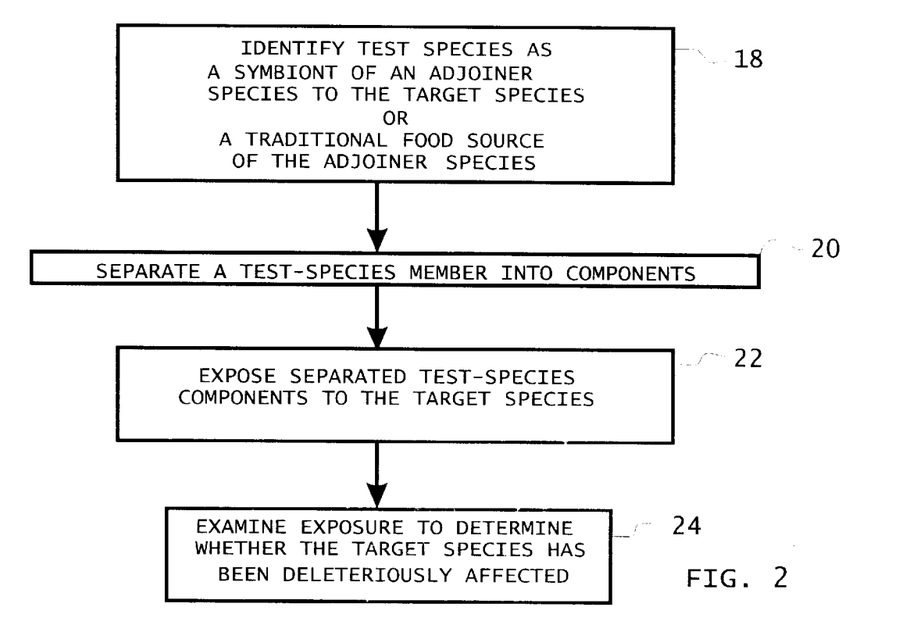
FIG. 2 is a block diagram of another preferred embodiment of the identification method of the present invention.

Referring to FIG. 2, another preferred embodiment of the method of the present invention of identifying components of members of a test species that deleteriously affect members of a target species that is a symbiont of a given adjoiner species includes a step 18 of identifying the test species as a symbiont or a co-evolutionary food source of the given adjoiner species when the test species had not been known to be a symbiont or a co-evolutionary food source of the given adjoiner species, respectively; a step 20 of separating at least one member of the test species into a plurality of components; a step 22 of exposing at least some of the separated components of the member(s) of the test species separately to members of the target species; and a step 24 of examining such exposures to determine for such identification whether members of the target species have been deleteriously affected by such exposures.

In some preferred embodiments of the methods described above, prior to the separation step 10, 20, the method includes a step (not shown) of exposing at least a component of the target species to at least one member of the test species for the purpose of establishing any immunity of such target-species component to the test species as may be established.

Figure 3:
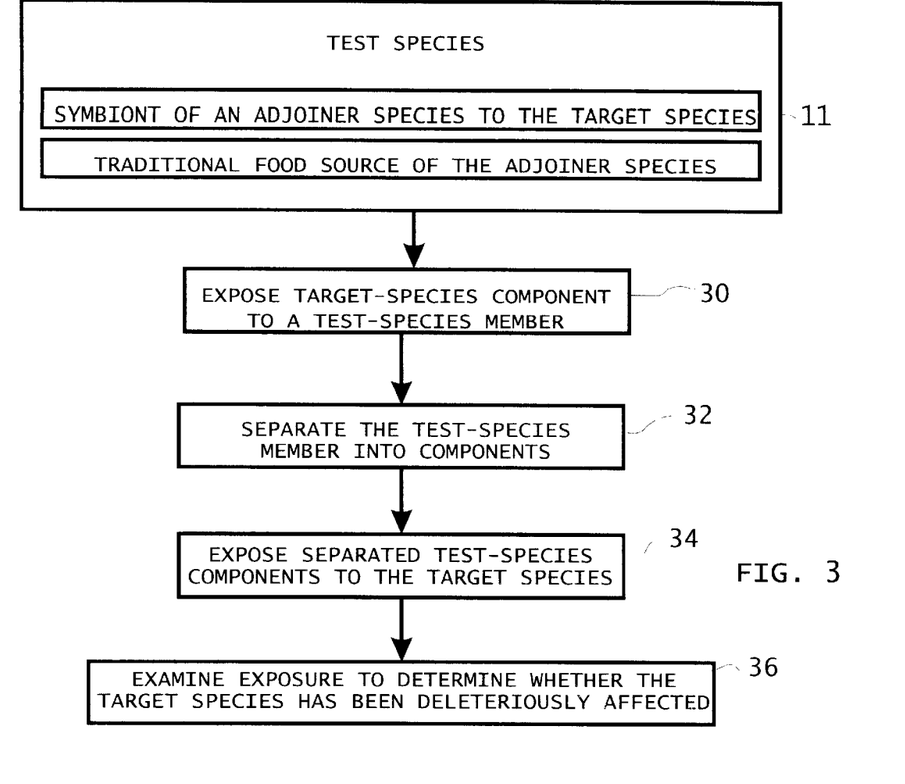
FIG. 3 is a block diagram of a further preferred embodiment of the identification method of the present invention.

Referring to FIG. 3, a further preferred embodiment of the method of the present invention of identifying components of members of a test species that deleteriously affect members of a target species that is a symbiont of a given adjoiner species includes a step 30 of exposing at least a component of at least one member of the target species to at least one member of a test species that is a symbiont or a traditional food source of the given adjoiner species; a subsequent step 32 of separating the exposed at least one member of the test species into a plurality of components; a step 34 of exposing at least some of the separated components of the member(s) of the test species separately to members of the target species; and a step 36 of examining such exposures to determine for such identification whether members of the target species have been deleteriously affected by such exposures. Preferably, this method further includes a step (not shown) of interposing a sufficient period of time between the first exposure step 30 and the separation step 32 to enable the exposed test species member(s) to react to the exposure of the target-species component to the test-species member.

In some embodiments of the above-described methods, members of the test species at least in some aspect deleteriously affect members of the adjoiner species.

In some embodiments of the above-described methods, members of the target species at least in some aspect deleteriously affect members of the adjoiner species.

Figure 4:
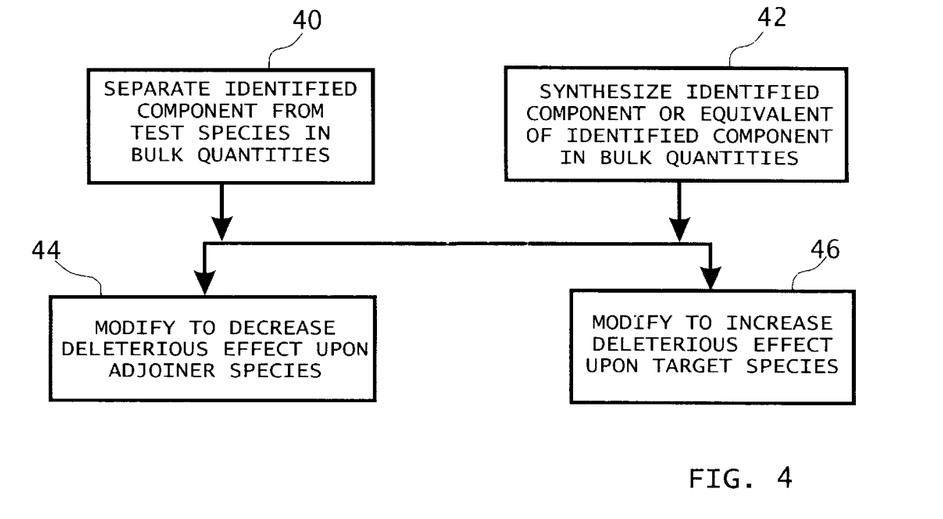
FIG. 4 is a block diagram showing preferred embodiments of product manufacturing methods according to the present invention

Preferred embodiments of methods according to the present invention of manufacturing a product including a test-species component identified by any of the above-described methods as deleteriously affecting members of a target species and/or an equivalent of said identified component are described with reference to FIG. 4. The product is manufactured either by a step 40 of separating the identified component in bulk quantities from said members of said test species or by a step 42 of synthesizing the identified component and/or an equivalent of the identified component in bulk quantities. The manufacturing method may further include a step 44 of modifying the product to decrease any deleterious effect upon the adjoiner species caused by the identified component and/or the equivalent of the identified component; and/or a step 46 of modifying the product to increase the deleterious effect upon the target species caused by the identified component and/or the equivalent of the identified component. The deleterious effect can be modified by varying the quantity of the identified component and/or the equivalent of the identified component within the product.

Figure 5:
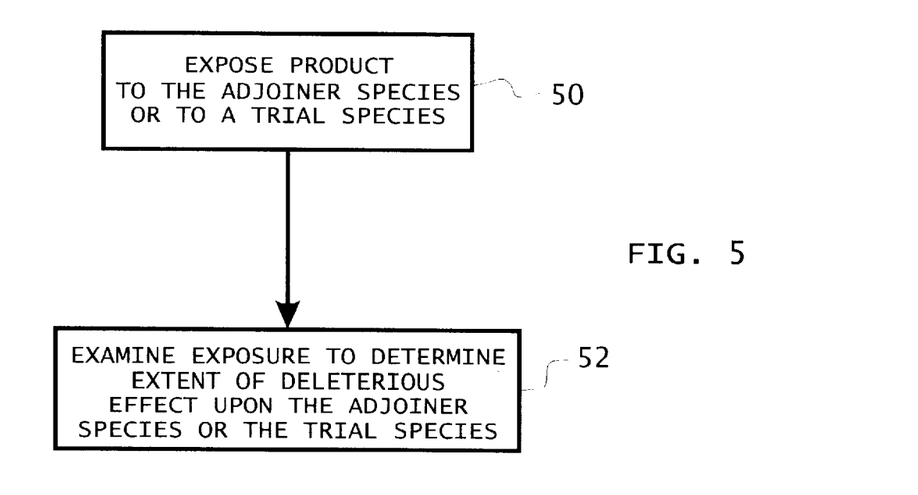
FIG. 5 is a block diagram of one preferred embodiment of a product testing method according to the present invention

Referring to FIG. 5, one preferred embodiment of a method according to the present invention of testing the above-described manufactured product, includes a step 50 of exposing the product to the adjoiner species or a member of a trial species; and a step 52 of examining such exposure to determine the extent of any deleterious effect upon the adjoiner species or the trial species respectively. Preferably, the trial species reacts to such exposure in a manner equivalent to such a reaction by the adjoiner species.

Figure 6:
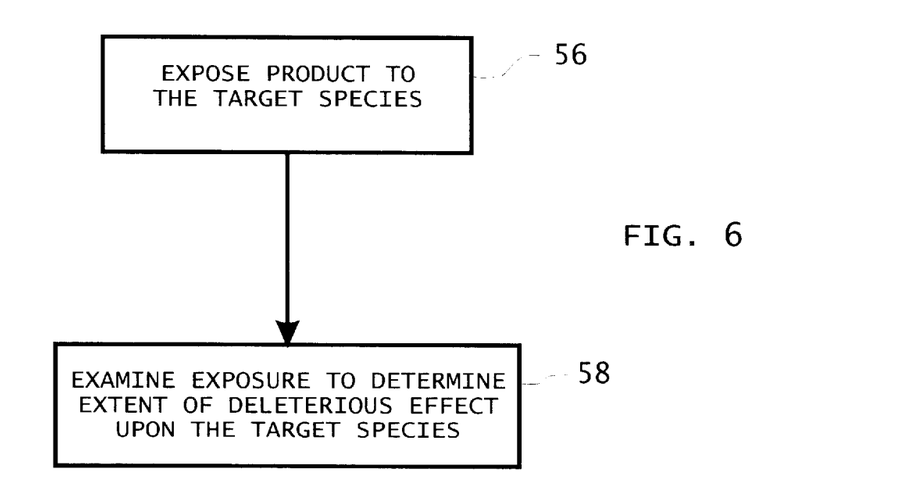
FIG. 6 is a block diagram of another preferred embodiment of a product testing method according to the present invention

Referring to FIG. 6, another preferred embodiment of a method according to the present invention of testing the above-described manufactured product, includes a step 56 of exposing the product to the target species; and a step 58 of examining such exposure to determine the extent of the deleterious effect upon the target species.

A preferred embodiment (not shown) of a method according to the present invention of using a component of a member of a test species identified by the any of the above-described methods and/or an equivalent of the identified component to treat an adjoiner species that is afflicted with a target species includes the step of exposing the identified component and/or the equivalent of the identified component to members of the target species that are residing in or on a member of the adjoiner species. Preferably, such exposure is accomplished by using a product manufactured by one of the above-described manufacturing methods.

In some, but not all, of the various embodiments of the deleterious-component identifying methods according to the present, it is preferred that during the step of exposing separated components of member(s) of the test species to members of the target species, the exposed members of the target species are isolated from the adjoiner species.

The advantages specifically stated herein do not necessarily apply to every conceivable embodiment of the present invention. Further, such stated advantages of the present invention are only examples and should not be construed as the only advantages of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

I claim:

1. A method of identifying components of members of test species that deleteriously affect members of a target species, comprising the steps of:

(a) separating at least one member of a test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (a), (b) and (c) are executed methodically and systematically with a large number of test species that are symbionts of the adjoiner species.

2. A method according to claim 1, wherein step (a) is executed with such a large number of test species that are symbionts of the adjoiner species that the ratio of execution of step (a) when the test species are symbionts of the adjoiner species relative to execution of step (a) when the test species are not symbionts of the adjoiner species is significantly higher than said ratio of execution according to the prior art.

3. A method of identifying components of members of test species that deleteriously affect members of a target species, comprising the steps of:

(a) separating at least one member of a test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein step (a) is executed with such a large number of test species that are symbionts of the adjoiner species that the ratio of execution of step (a) when the test species are symbionts of the adjoiner species relative to execution of step (a) when the test species are not symbionts of the adjoiner species is significantly higher than said ratio of execution according to the prior art.

4. A method according to claim 1 or 3, wherein steps (b) and (c) are executed in such large numbers when the test species are symbionts of the adjoiner species that the ratio of execution of steps (b) and (c) when the test species are symbionts of the adjoiner species relative to execution of steps (b) and (c) when the test species are not symbionts of the adjoiner species is significantly higher than said ratio of execution according to the prior art.

5. A method of identifying components of members of test species that deleteriously affect members of a target species, comprising the steps of:

(a) separating at least one member of each of a plurality of test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (b) and (c) are executed in such large numbers when the test species are symbionts of the adjoiner species that the ratio of execution of steps (b) and (c) when the test species are symbionts of the adjoiner species relative to execution of steps (b) and (c) when the test species are not symbionts of the adjoiner species is significantly higher than said ratio of execution according to the prior art.

6. A method of identifying components of members of a test species that deleteriously affect members of a target species, comprising the steps of:

(a) separating at least one member of the test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (b) and (c) are executed in such large numbers when the test species is a symbiont of the adjoiner species that the ratio of execution of steps (b) and (c) when the test species is a symbiont of the adjoiner species relative to execution of steps (b) and (c) when the test species is not a symbiont of the adjoiner species is significantly higher than said ratio of execution according to the prior art.

7. A method according to claim 1, 3, 5 or 6, further comprising the step of:

(d) prior to step (a), identifying the test species as a symbiont of the given adjoiner species when the test species had not been known to be a symbiont of the given adjoiner species.

8. A method of identifying components of members of a test species that deleteriously affect members of a target species, comprising the steps of:.

(a) identifying the test species as a symbiont of a given adjoiner species when the test species had not been known to be a symbiont of the given adjoiner species;

(b) separating at least one member of the test species into a plurality of components;

(c) exposing at least some of said separated components of said member(s) of the test species separately to members of the target species, wherein the target species is a symbiont of the adjoiner species; and (d) examining said exposures to determine for said identification whether members of the target species have been deleteriously affected by said exposures.

9. A method according to claim 1, 3, 6 or 8, further comprising the step of:

(e) prior to said separation step, exposing at least a component of the target species to at least one member of the test species.

10. A method of identifying components of members of a test species that deleteriously affect members of a target species, comprising the steps of:

(a) exposing at least a component of at least one member of the target species to at least one member of the test species;

(b) subsequent to step (a), separating said exposed at least one member of the test species into a plurality of components;

(c) exposing at least some of said separated components of said member(s) of the test species separately to members of the target species, wherein the target species is a symbiont of an adjoiner species and the test species is a symbiont of the adjoiner species; and (d) examining said exposures to determine for said identification whether members of the target species have been deleteriously affected by said exposures.

11. A method of identifying components of members of test species that deleteriously affect members of a target species, comprising the steps of:

(a) separating at least one member of a test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (a), (b) and (c) are executed methodically and systematically with a large number of test species that are traditional food sources of the adjoiner species.

12. A method according to claim 11, wherein step (a) is executed with such a large number of test species that are traditional food sources of the adjoiner species that the ratio of execution of step (a) when the test species are traditional food sources of the adjoiner species relative to execution of step (a) when the test species are not traditional food sources of the adjoiner species is significantly higher than said ratio of execution according to the prior art.

13. A method of identifying components of members of test species that deleteriously affect members of a target species, comprising the steps of:

(a) separating at least one member of a test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein step (a) is executed with such a large number of test species that are traditional food sources of the adjoiner species that the ratio of execution of step (a)

when the test species are traditional food sources of the adjoiner species relative to execution of step (a) when the test species are not traditional food sources of the adjoiner species is significantly higher than said ratio of execution according to the prior art.

14. A method according to claim 11 or 13, wherein steps (b) and (c) are executed in such large numbers when the test species are traditional food sources of the adjoiner species that the ratio of execution of steps (b) and (c) when the test species are traditional food sources of the adjoiner species relative to execution of steps (b) and (c) when the test species are not traditional food sources of the adjoiner species is significantly higher than said ratio of execution according to the prior art.

15. A method of identifying components of members of test species that deleteriously affect members of a target species, comprising the steps of:

(a) separating at least one member of each of a plurality of test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (b) and (c) are executed in such large numbers when the test species are traditional food sources of the adjoiner species that the ratio of execution of steps (b) and (c) when the test species are traditional food sources of the adjoiner species relative to execution of steps (b) and (c) when the test species are not traditional food sources of the adjoiner species is significantly higher than said ratio of execution according to the prior art.

16. A method of identifying components of members of a test species that deleteriously affect members of a target species, comprising the steps of:

(a) separating at least one member of the test species into a plurality of components;

(b) exposing at least some of said separated components of said member(s) of the test species separately to members of the target species, wherein the target species is a symbiont of an adjoiner species; and (c) examining said exposures to determine for said identification whether members of the target species have been deleteriously affected by said exposures;

wherein steps (b) and (c) are executed in such large numbers when the test species is a traditional food source of the adjoiner species that the ratio of execution of steps (b) and (c) when the test species is a traditional food source of the adjoiner species relative to execution of steps (b) and (c) when the test species is not a traditional food source of the adjoiner species is significantly higher than said ratio of execution according to the prior art.

17. A method according to claim 11, 13, 15 or 16, further comprising the step of:

(d) prior to step (a), identifying the test species as a co-evolutionary food source of the given adjoiner species when the test species had not been known to be a co-evolutionary food source of the given adjoiner species.

18. A method of identifying components of members of a test species that deleteriously affect members of a target species, comprising the steps of:

(a) identifying the test species as a co-evolutionary food source of the given adjoiner species when the test species had not been known to be a co-evolutionary food source of the given adjoiner species;

(b) separating at least one member of the test species into a plurality of components;

(c) exposing at least some of said separated components of said member(s) of the test species separately to members of the target species, wherein the target species is a symbiont of the adjoiner species; and (d) examining said exposures to determine for said identification whether members of the target species have been deleteriously affected by said exposures.

19. A method according to claim 11, 13, 16 or 18, further comprising the step of:

(e) prior to said separation step, exposing at least a component of the target species to at least one member of the test species.

20. A method of identifying components of members of a test species that deleteriously affect members of a target species, comprising the steps of:

(a) exposing at least a component of at least one member of the target species to at least one member of the test species;

(b) subsequent to step (a), separating said exposed at least one member of the test species into a plurality of components;

(c) exposing at least some of said separated components of said member(s) of the test species separately to members of the target species, wherein the target species is a symbiont of an adjoiner species and the test species is a traditional food source of the adjoiner species; and (d) examining said exposures to determine for said identification whether members of the target species have been deleteriously affected by said exposures.

21. A method according to any of claims 1, 3, 5, 6, 8, 10, 11, 13, 15, 16, 18 or 20, wherein the adjoiner species is the human species.

22. A method according to any of claims 1, 3, 5, 6, 8, 10, 11, 13, 15, 16, 18 or 20, wherein the adjoiner species has a near-human-species genetic composition.

23. A separated component of a member of a test species identified by the method of any of claims 1, 3, 5, 6, 8, 10, 11, 13, 15, 16, 18 or 20 as deleteriously affecting members of a target species or an equivalent of said identified component.

24. A method of using a component of a member of a test species identified by the method of any of claims 1, 3, 5, 6, 8, 10, 11, 13, 15, 16, 18 or 20 as deleteriously affecting members of a target species and/or an equivalent of said identified component, comprising the step of:

(e) exposing said identified component and/or an equivalent of said identified component to members of the target species that are residing in or on a member of the adjoiner species.

25. A method of manufacturing a product including a test-species component identified by the method of any of claims 1, 3, 5, 6, 8, 10, 11, 13, 15, 16, 18 or 20 as deleteriously affecting members of a target species and/or an equivalent of said identified component, comprising the step of:

(e) providing said component in bulk quantities.

26. A product manufactured according to the method of claim 25.

27. A method according to claim 25, further comprising the step of:

(f) modifying the product to decrease any deleterious effect upon the adjoiner species caused by the identified component and/or said equivalent thereof.

28. A product manufactured according to the method of claim 27.

29. A method according to claim 25, further comprising the step of:

(f) modifying the product to increase the deleterious effect upon the target species caused by the identified component and/or said equivalent thereof.

30. A product manufactured according to the method of claim 29.

31. A method according to claim 25, wherein step (e) comprises separating said component in bulk quantities from said members of said test species.

32. A product manufactured according to the method of claim 31.

33. A method according to claim 25, wherein step (e) comprises synthesizing said component and/or an equivalent thereof in bulk quantities.

34. A product manufactured according to the method of claim 33.

35. A method of testing a product manufactured according to claim 25, comprising the steps of:

(f) exposing said product to the adjoiner species or a member of a trial species; and (g) examining said exposure of step (f) to determine the extent of any deleterious effect upon the adjoiner species or the trial species respectively.

36. A method of testing a product manufactured according to claim 25, comprising the steps of:

(f) exposing said product to the target species; and (g) examining said exposure of step (f) to determine the extent of the deleterious effect upon the target species.

37. A method according to claim 10 or 20, further comprising the step of:

(e) interposing a sufficient period of time between steps (a) and (b) to enable said exposed test species member (s) to react to said exposure of step (a).

38. A method according to claims 1, 3, 5, 6, 8, 10, 11, 13, 15, 16, 18 or 20, wherein members of the test species at least in some aspect deleteriously affect members of the adjoiner species.

39. A method according to claims 1, 3, 5, 6, 8, 10, 11, 13, 15, 16, 18 or 20, wherein members of the target species at least in some aspect deleteriously affect members of the adjoiner species.

40. A method according to claims 1, 3, 5, 6, 8, 10, 11, 13, 15, 16, 18 or 20, wherein during said step of exposing separated components of member(s) of said test species to members of the target species, said exposed members of the target species are isolated from the adjoiner species.

* * * * *

(12) EX PARTE REEXAMINATION CERTIFICATE (9952nd)

United States Patent
Sorensen (10) Number: US 5,843,698 C1
(45) Certificate Issued: Nov. 21, 2013

(54) DELETERIOUSLY AFFECTING MEMBERS OF A TARGET SPECIES BY EXPOSURE TO A COMPONENT OF SYMBIONT OR FOOD SOURCE OF AN ADJOINER SPECIES THAT IS SYMBIOTIC WITH THE TARGET SPECIES

(75) Inventor: Jens Ole Sorensen, Cayman Kai (KY)

(73) Assignee: Sorensen Research and Development Trust, San Diego, CA (US)

Reexamination Request:
No. 90/011,651, Apr. 20, 2011

Reexamination Certificate for:
| | |
|---|---|
| Patent No.: | 5,843,698 |
| Issued: | Dec. 1, 1998 |
| Appl. No.: | 08/846,670 |
| Filed: | Apr. 30, 1997 |

(51) Int. Cl.
*C12Q 1/00* (2006.01)
*C12Q 1/02* (2006.01)

(52) U.S. Cl.
USPC .......... 435/29; 426/231; 426/665; 435/253.1; 435/253.3; 435/4; 435/5; 435/7.21; 435/7.22; 435/7.23

(58) Field of Classification Search
None
See application file for complete search history.

(56) References Cited

To view the complete listing of prior art documents cited during the proceeding for Reexamination Control Number 90/011,651, please refer to the USPTO's public Patent Application Information Retrieval (PAIR) system under the Display References tab.

*Primary Examiner* — Sharon Turner (57) ABSTRACT

A component of a member of a test species that deleteriously affects a target species that is a parasite of a given adjoiner species is identified by a method including a step (a) of separating at least one member of a test species that is a symbiont or a traditional food source of the given adjoiner species into a plurality of components; a step (b) of exposing at least some of the separated components of the member(s) of the test species separately to members of the target species; and a step (c) of examining such exposures to determine for such identification whether members of the target species have been deleteriously affected by such exposures; wherein steps (a), (b) and (c) are executed methodically and systematically. A product including such a test-species component identified as deleteriously affecting members of a target species and/or an equivalent of the identified component is manufactured either by separating the identified component in bulk quantities from members of the test species or by synthesizing the identified component and/or an equivalent of the identified component in bulk quantities. The product is tested to determine the extent of any deleterious effect upon the adjoiner species and the extent of the deleterious effect of the product upon the target species. The method of manufacturing the product may further include modifying the product to decrease any deleterious effect upon the adjoiner species and/or modifying the product to increase the deleterious effect upon the target species.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-40 are cancelled.

\* \* \* \* \*